(12) United States Patent
Mead et al.

(10) Patent No.: US 10,861,193 B2
(45) Date of Patent: Dec. 8, 2020

(54) METHOD OF CALIBRATING A PATIENT MONITORING SYSTEM FOR USE WITH A RADIOTHERAPY TREATMENT APPARATUS

(71) Applicant: VISION RT LIMITED, London (GB)

(72) Inventors: Edward Mead, London (GB); Ivan Meir, London (GB)

(73) Assignee: VISION RT LTD., London (GB)

( * ) Notice: Subject to any disclaimer, the term of this patent is extended or adjusted under 35 U.S.C. 154(b) by 122 days.

(21) Appl. No.: 15/516,628

(22) PCT Filed: Sep. 29, 2015

(86) PCT No.: PCT/GB2015/052819
§ 371 (c)(1),
(2) Date: Apr. 3, 2017

(87) PCT Pub. No.: WO2016/051153
PCT Pub. Date: Apr. 7, 2016

(65) Prior Publication Data
US 2018/0232910 A1    Aug. 16, 2018

(30) Foreign Application Priority Data

Oct. 2, 2014  (GB) .................................. 1417468.4

(51) Int. Cl.
*G06T 7/80* (2017.01)
*A61N 5/10* (2006.01)
(Continued)

(52) U.S. Cl.
CPC .............. *G06T 7/85* (2017.01); *A61N 5/1049* (2013.01); *A61N 5/1075* (2013.01);
(Continued)

(58) Field of Classification Search
CPC .. G06T 7/85; G06T 7/70; G06T 5/006; G06T 5/50; G06T 17/20; G06T 2200/04;
(Continued)

(56) References Cited

U.S. PATENT DOCUMENTS 6,032,066 A * 2/2000 Lu ............................ A61B 6/08
128/920
7,348,974 B2   3/2008 Smith et al.
(Continued)

FOREIGN PATENT DOCUMENTS

| WO | 2014057280 A1 | 4/2014 |
| WO | 2014102929 A1 | 7/2014 |
| WO | 2015008040 A2 | 1/2015 |

OTHER PUBLICATIONS

International Search Report and the Written Opinion of the International Searching Authority dated Apr. 6, 2016 to International Application No. PCT/GB2015/052819.
(Continued)

*Primary Examiner* — Pinalben Patel
(74) *Attorney, Agent, or Firm* — Birch, Stewart, Kolasch & Birch, LLP

(57) ABSTRACT

A calibration sheet is located at a first position where its surface substantially corresponds to the expected position of a patient surface lying on a mechanical couch during treatment. Images of the calibration sheet are obtained and processed to ascertain relative locations and orientations of the image detectors obtaining the images and optical distortion parameters indicative of optical distortions present in the obtained images of the calibration sheet. The calibration sheet is then re-located to a known position relative to the iso-centre of the treatment apparatus and images of the re-located calibration sheet are obtained and processed to determine a transform corresponding to the relocation of the calibration sheet from the first position to the iso-centre of
(Continued)

the treatment apparatus. Data indicative of optical distortions present in the images and data indicative of the locations and orientations of the image detectors relative to the iso-centre of the treatment apparatus are stored.

9 Claims, 6 Drawing Sheets

(51) Int. Cl.
*G06T 7/70* (2017.01)
*G06K 9/32* (2006.01)
*G06T 5/00* (2006.01)
*G06T 5/50* (2006.01)
*G06T 17/20* (2006.01)
*H04N 13/243* (2018.01)

(52) U.S. Cl.
CPC ............ *G06K 9/3216* (2013.01); *G06T 5/006* (2013.01); *G06T 5/50* (2013.01); *G06T 7/70* (2017.01); *G06T 17/20* (2013.01); *A61N 2005/1059* (2013.01); *G06T 2200/04* (2013.01); *G06T 2200/08* (2013.01); *G06T 2207/10028* (2013.01); *G06T 2207/30004* (2013.01); *G06T 2207/30196* (2013.01); *H04N 13/243* (2018.05)

(58) Field of Classification Search
CPC ....... G06T 2200/08; G06T 2207/10028; G06T 2207/30004; G06T 2207/30196; A61N 5/1049; A61N 5/1075; A61N 2005/1059; G06K 9/3216; H04N 13/243
See application file for complete search history.

(56) References Cited

U.S. PATENT DOCUMENTS

| | | | |
|---|---|---|---|
| 7,889,906 B2 | 2/2011 | Smith et al. | |
| 7,889,907 B2 | 2/2011 | Engelbart et al. | |
| 8,135,201 B2 | 3/2012 | Smith et al. | |
| 8,198,579 B2* | 6/2012 | Jeung | A61B 6/08 250/252.1 |
| 9,230,322 B2* | 1/2016 | Hirai | G06T 7/0012 |
| 2003/0218607 A1* | 11/2003 | Baumberg | G06T 15/20 345/419 |
| 2006/0079757 A1* | 4/2006 | Smith | A61N 5/1049 600/416 |
| 2006/0122502 A1* | 6/2006 | Scherch | A61B 6/0492 600/426 |
| 2009/0187112 A1 | 7/2009 | Meir et al. | |
| 2009/0285357 A1* | 11/2009 | Khamene | A61B 6/08 378/20 |
| 2011/0301449 A1* | 12/2011 | Maurer, Jr. | A61B 6/032 600/411 |
| 2013/0010081 A1* | 1/2013 | Tenney | A61B 34/30 348/47 |
| 2013/0229495 A1* | 9/2013 | Bani-Hashemi | A61B 6/582 348/47 |
| 2017/0027540 A1* | 2/2017 | Sjolund | A61B 6/583 |

OTHER PUBLICATIONS

Combined Search and Examination Report under Sections 17 and 18(3) dated Mar. 16, 2015 in GB Application No. GB1417468.4.
Hadley, S.W. et al., "Calibration of video cameras to the coordinate system of a radiation therapy treatment machine", GCC 2004, Lecture notes in computer science, ISSN 0302-9743, vol. 3251, pp. 223-231.
Tsai, R., "A versatile camera calibration technique for high-accuracy 3D machine vision metrology using off-the-shelf TV cameras and lenses", IEEE Journal on Robotics and Automation, USA, vol. 3, No. 4, Aug. 1, 1987, pp. 323-344.

* cited by examiner

METHOD OF CALIBRATING A PATIENT MONITORING SYSTEM FOR USE WITH A RADIOTHERAPY TREATMENT APPARATUS

CROSS REFERENCE TO RELATED APPLICATION

This application is a National Phase filing under 35 C.F.R. § 371 of and claims priority to PCT Patent Application No.: PCT/GB2015/052819, filed on Sep. 29, 2015, which claims the priority benefit under 35 U.S.C. § 119 of British Application No.: 1417468.4, filed on Oct. 2, 2014, the contents of which are hereby incorporated in their entireties by reference.

The present invention concerns a method of calibrating a patient monitoring system. In particular, embodiments of the present invention concern a method of calibrating a patient monitoring system for use with a radiotherapy treatment apparatus and the like where accurate positioning and the detection of patient movement is important for successful treatment.

Radiotherapy consists of projecting onto a predetermined region of a patient's body, a radiation beam so as to destroy or eliminate tumours existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

When applying radiation to a patient, the gating of treatment apparatus should be matched with the breathing cycle so that radiation is focused on the location of a tumour and collateral damage to other tissues is minimised. If movement of a patient is detected the treatment should be halted to avoid irradiating areas of a patient other than a tumour location.

For this reason a number of monitoring systems for assisting the positioning of patients during radiotherapy have therefore been proposed such as those described in Vision RT's earlier patents and patent applications U.S. Pat. Nos. 7,889,906, 7,348,974, 8,135,201, 9,028,422, US2015/0216450, WO2014/057280, and WO2015/008040 all of which are hereby incorporated by reference.

In the systems described in Vision RT's patent applications, stereoscopic images of a patient are obtained and processed to generate data identifying 3D positions of a large number of points corresponding to points on the surface of an imaged patient. Such data can be compared with data generated on a previous occasion and used to position a patient in a consistent manner or provide a warning when a patient moves out of position. Typically such a comparison involves undertaking Procrustes analysis to determine a transformation which minimises the differences in position between points on the surface of a patient identified by data generated based on live images and points on the surface of a patient identified by data generated on a previous occasion.

Treatment plans for the application of radiotherapy are becoming increasingly complex with treatment apparatus having multiple or floating iso-centres. Also, there is an increasing trend to make use of higher doses of radiation during treatment in order to reduce overall treatment time. Such increasing complexity and higher dosages bring with them the increasing possibility of mistreatment. There is therefore an ever increasing need for improvements in the accuracy of patient monitoring systems.

In accordance with one aspect of the present invention, a method of calibrating a patient monitoring system comprising a plurality of image detectors arranged to view the surface of a patient lying on a mechanical couch of a radio therapy treatment apparatus is provided.

In accordance with the present invention, initially, a calibration object is located at a first position where the surface of the calibration object substantially corresponds to the expected position of a surface a patient lying on the mechanical couch of the radio therapy treatment apparatus during treatment as viewed by image detectors of the patient monitoring system being calibrated. Images of the calibration object are then obtained using the image detectors and the images are processed to ascertain the relative locations and orientations of the image detectors and lens distortion parameters indicative of optical image distortions present in the images obtained by the image detectors. The calibration object is then re-located to a second position at a known position relative to the iso-centre of the treatment apparatus and images of the re-located calibration object are then obtained using the plurality of image detectors. The obtained images are then processed to determine a transform corresponding to the relocation of the calibration object from the first position to the iso-centre of the treatment apparatus and data indicative of optical image distortions present in the images obtained by the image detectors of the calibration object in the first position, and data indicative of the locations and orientations of the image detectors relative to the iso-centre of the treatment apparatus are determined by applying said determined transformation to the ascertained relative locations and orientations of the image detectors is then stored.

Once the patient monitoring system has been calibrated, images of a patient lying on the mechanical couch of the radio therapy treatment apparatus can be obtained using the plurality of image detectors and processed utilising the stored data indicative of optical image distortions present in images obtained by the image detectors, and data indicative of the locations and orientations of the image detectors relative to the iso-centre of the treatment apparatus to create a model of the surface the patient.

Alternatively, a plurality of calibrations of the patient monitoring system can be implemented in accordance with the present invention, with each of the plurality of calibrations being implemented with the calibration object located at a different first position. The data stored as a result of each of the plurality of calibrations would then further comprise an indication of the location of the first position used for the corresponding calibration. The position of a surface of the patient to be monitored can then be determined, and the determined position used to select the data stored as a result of the calibration for which the location of the first position used for the calibration corresponds to the position of the surface of the patient. Images of the patient lying on the mechanical couch of the radio therapy treatment apparatus can then be obtained using the plurality of image detectors, and processed utilising the selected data to generate a model of the surface of the patient.

The applicants have appreciated that there are two distinct aspects to calibrating a patient monitoring system. In order to facilitate the positioning of a patient relative to the iso-centre of a treatment apparatus, it is important to be able to identify the relative locations of image detectors monitoring a patient both relative to each other and relative to the iso-centre of the treatment apparatus. Separate from this calibration, it is also necessary to identify any optical distortions present in images obtained by the image detectors so as to account for such distortions when generating models of a patient being monitored. The applicants believe that calibrating intrinsic parameters (i.e. data indicative of optical image distortions present in the images obtained by the image detectors) based on images corresponding to a surface at the expected location of the surface a patient being monitored should increase the accuracy with which such optical distortions can be accounted for when monitoring a patient and hence improve the accuracy of the patient monitoring system.

In some embodiments the patient monitoring system may comprise a single stereoscopic camera having a plurality of image detectors. In other embodiments the patient monitoring system may comprise a plurality of stereoscopic cameras each having a plurality of image detectors. Where the patient monitoring system comprises a plurality of stereoscopic cameras, images from each of the plurality of stereoscopic cameras may be processed to determine a transform corresponding to the re-location of the calibration object from the first position to the iso-centre of the treatment apparatus for each individual stereoscopic camera and an average transform corresponding to the relocation of the calibration object from the first position to the iso-centre of the treatment apparatus may be determined. Alternatively an individual stereoscopic camera may be selected and images from just that stereoscopic camera may be obtained and processed to determine a transform corresponding to the relocation of the calibration object from the first position to the iso-centre of the treatment apparatus.

In the case of a patient monitoring system involving a plurality of stereoscopic cameras, the transform calculated corresponding to the relocation of the calibration object from the first position to the iso-centre of the treatment apparatus should be identical for all of the stereoscopic cameras. However, in practice, there are normally some inaccuracies such that there will be differences between transforms calculated for individual stereoscopic cameras. By determining and applying the average of the transforms to the overall system, this approach ensures that the same transform is used for each camera system, avoiding any divergence, whilst also making use of the average to apply a "best-fit" that should minimise the error.

Alternatively, a transform could be determined for just one of the stereoscopic cameras, and that transform applied to all of the camera systems. Whilst this would avoid any divergence, this approach is less likely to reduce the overall error.

Embodiments of the present invention will now be described with reference to the accompanying drawings in which.

Prior to describing a method of calibration of a stereoscopic camera system that improves the accuracy of a patient monitoring system, the patient monitoring system and a radiotherapy treatment apparatus will be described.

Figure 1:
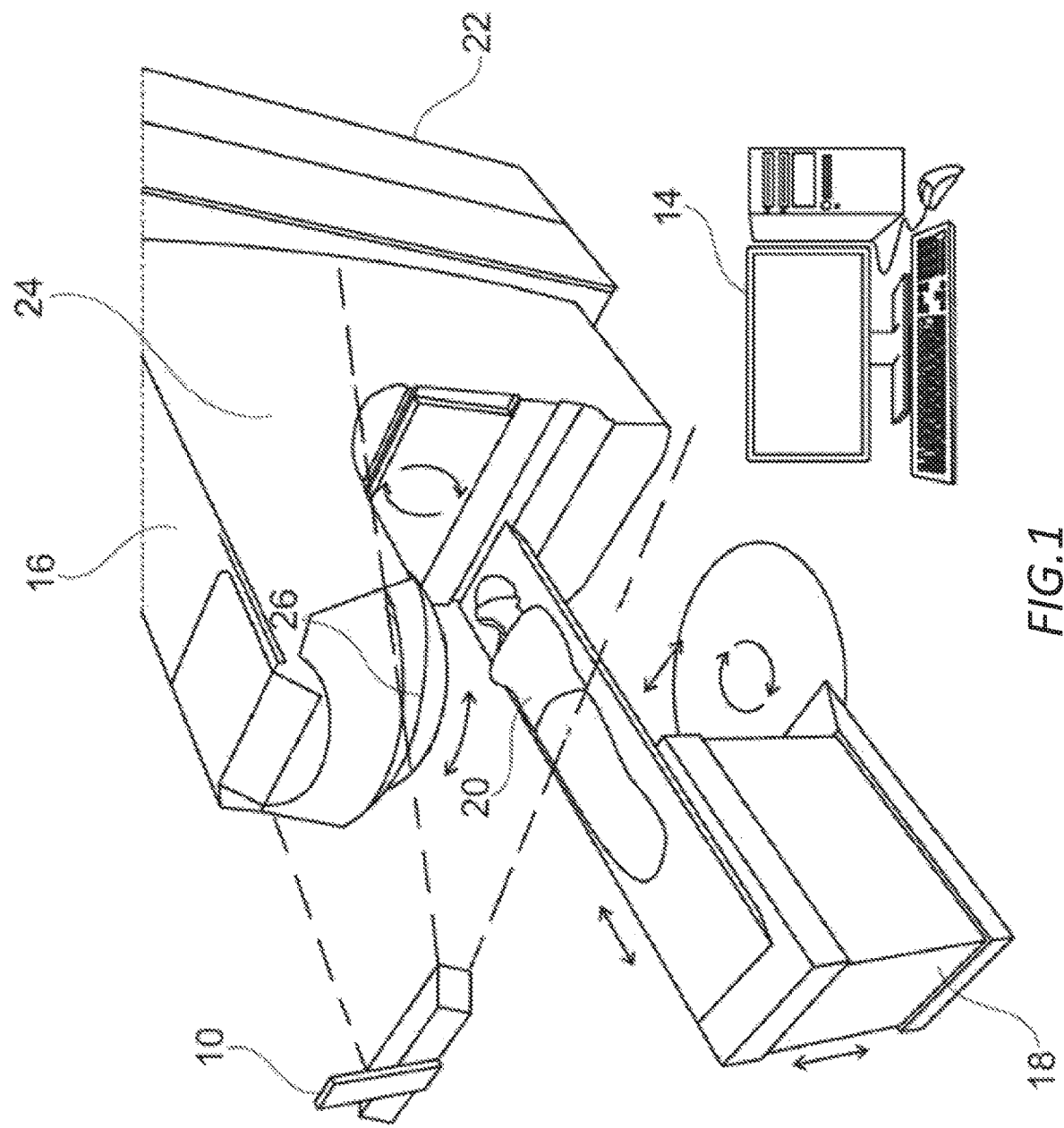
FIG. 1 is a schematic perspective view of a patient monitor.

FIG. 1 is a schematic perspective view of an embodiment of a patient monitoring system. In accordance with this embodiment, there is provided a stereoscopic camera system 10 that is connected by wiring (not shown) to a computer 14. The computer 14 is also connected to treatment apparatus 16 such as a linear accelerator for applying radiotherapy. A mechanical couch 18 is provided as part of the treatment apparatus upon which a patient 20 lies during treatment. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

The treatment apparatus 16 comprises a main body 22 from which extends a gantry 24. A collimator 26 is provided at the end of the gantry 24 remote from the main body 22 of the treatment apparatus 16. To vary the angles at which radiation irradiates a patient 20, the gantry 24, under the control of the computer 14, is arranged to rotate about an axis passing through the centre of the main body 22 of the treatment apparatus 16. Additionally the location of irradiation by the treatment apparatus may also be varied by rotating the collimator 26 at the end of the gantry 24.

Whilst the stereoscopic camera system 10 illustrated in FIG. 1 is comprised of a single stereoscopic camera, the stereoscopic camera system 10 could also be comprised of a set of stereoscopic cameras that are each orientated to obtain images of a patient 20 lying on the mechanical couch 18. For example, the stereoscopic camera system 10 could be comprised of two or three stereoscopic cameras distributed around the treatment apparatus 16.

In use, the image detectors of the stereoscopic camera system 10 obtain video images of a patient 20 lying on the mechanical couch 18. These video images are passed via the wiring to the computer 14. The computer 14 then processes the images of the patient 20 to generate a model of the surface of the patient. This model is compared with a model of the patient generated during earlier treatment sessions. When positioning a patient the difference between a current model surface and a target model surface obtained from an earlier session is identified and the positioning instructions necessary to align the surfaces are determined and sent to the mechanical couch 18. Subsequently during treatment any deviation from an initial set up can be identified and if the deviation is greater than a threshold, the computer 14 sends instructions to the treatment apparatus 16 to cause treatment to be halted until a patient 20 can be repositioned.

Figure 2:
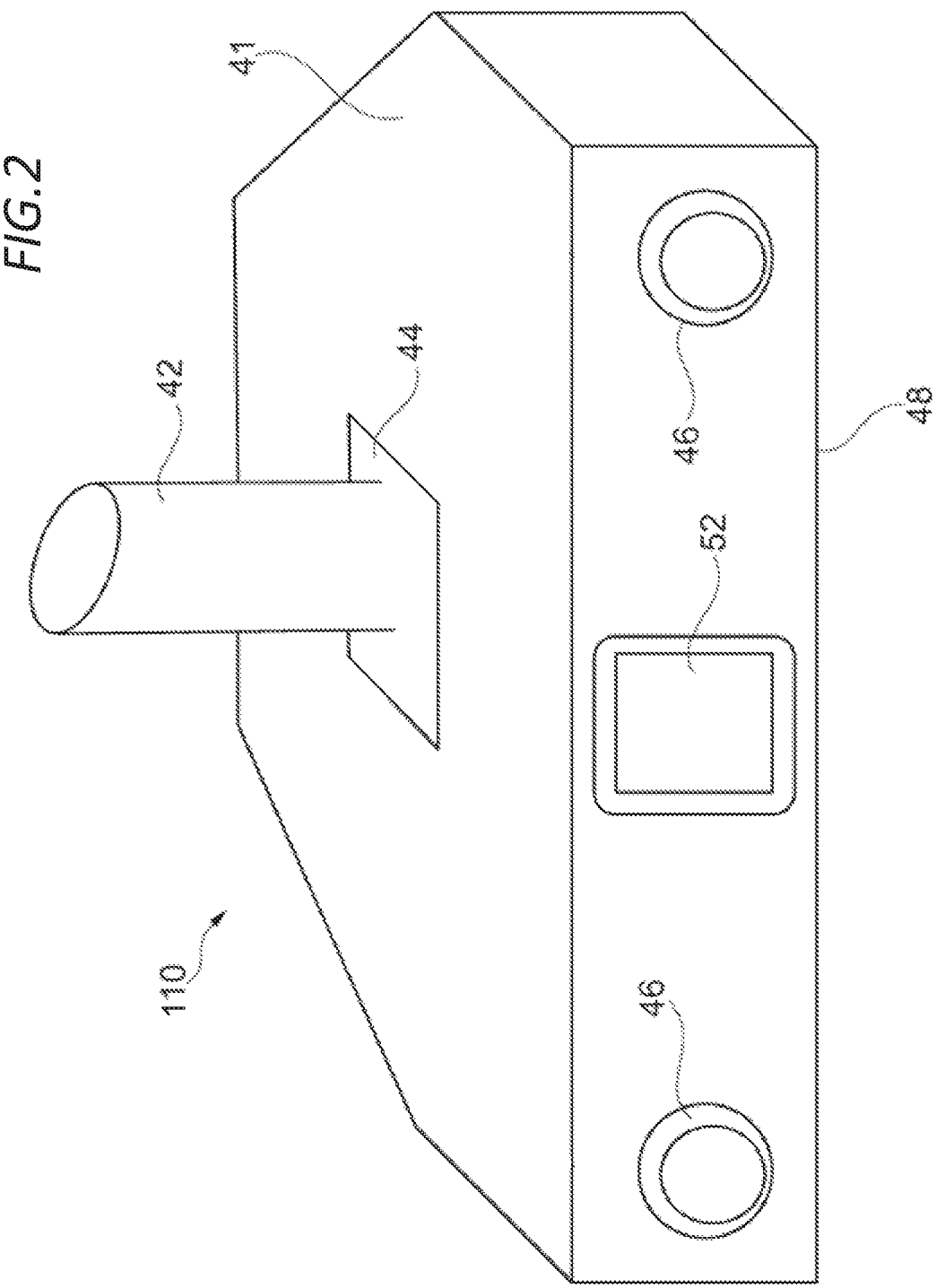
FIG. 2 is a front perspective view of the camera system of the patient monitor of FIG. 1.

FIG. 2 is a front perspective view of a stereoscopic camera 110 of a stereoscopic camera system 10 of the patient monitoring system of FIG. 1.

In this embodiment the stereoscopic camera 110 comprises a housing 41 which is connected to a bracket 42 via a hinge 44. The bracket 42 enables the stereoscopic 110 to be attached in a fixed location to the ceiling of a treatment room whilst the hinge 44 permits the stereoscopic camera 110 to be orientated relative to the bracket 42 so that the stereoscopic camera 110 is arranged to view a patient 20 on a mechanical couch 18.

A pair of lenses 46 are mounted at either end of the front surface 48 of the housing 41. These lenses 46 are positioned in front of image detectors such as CMOS active pixel sensors or charge coupled devices (not shown) contained within the housing 41. The image detectors are arranged behind the lenses 46 so as to capture images of a patient 20 via the lenses 46.

A speckle projector 52 is provided in the middle of the front surface 48 of the housing 41 between the two lenses 46. The speckle projector 52 is arranged to illuminate a patient 20 with a non-repeating speckled pattern of red light so that when images of a patient 20 are captured by the two image detectors corresponding portions of captured images can be distinguished. To that end the speckle projector comprises a light source such as a LED and a film with a random speckle pattern printed on the film. In use light from the light source is projected via the film and as a result a pattern consisting of light and dark areas is projected onto the surface of a patient 20. When images of the projected speckle pattern are captured by the stereoscopic camera 110 the images can then be processed to determine the positions of a set of points on the surface of the patient and hence the positioning of the patient can be monitored.

Figure 3:
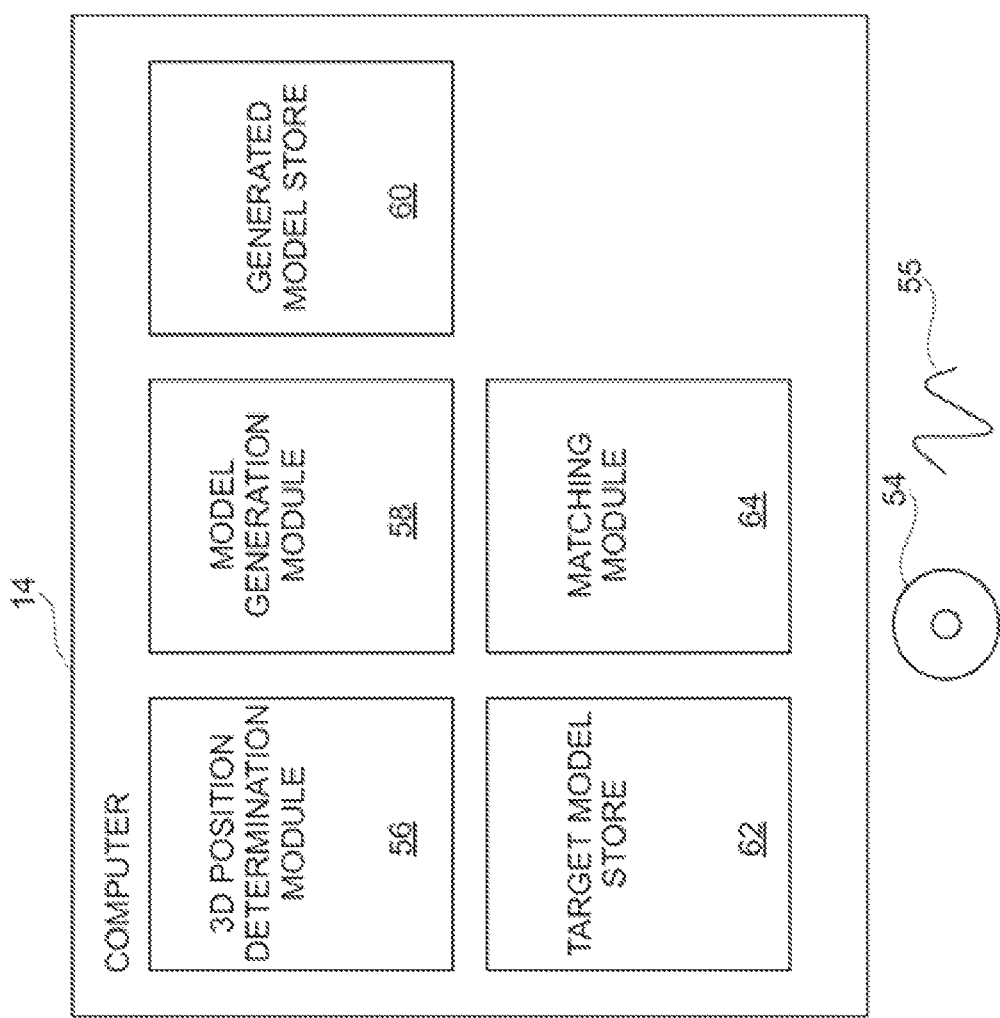
FIG. 3 is a schematic block diagram of the computer system of the patient monitor of FIG. 1.

FIG. 3 is a schematic block diagram of the computer 14 of the patient monitor of FIG. 1.

In order for the computer 14 to process images received from the stereoscopic camera system 10, the computer 14 is configured by software either provided on a disk 54 or by receiving an electrical signal 55 via a communications network into a number of functional modules 56-64. It will be appreciated that the functional modules 56-64 illustrated in FIG. 3 are purely notional in order to assist with the understanding of the working of the claimed invention and may not in certain embodiments directly correspond with blocks of code in the source code for the software. In other embodiments the functions performed by the illustrated functional modules 56-64 may be divided between different modules or may be performed by the re-use of the same modules for different functions.

In this embodiment, the functional modules 56-64 comprise: a 3D position determination module 56 for processing images received from the stereoscopic camera system 10, a model generation module 58 for processing data generated by the 3D position determination module 56 and converting the data into a 3D wire mesh model of an imaged computer surface; a generated model store 60 for storing a 3D wire mesh model of an imaged surface; a target model store 62 for storing a previously generated 3D wire mesh model; and a matching module 64 for determining rotations and translations required to match a generated model with a target model.

In use, as images are obtained by the stereoscopic camera system 10, these images are processed by the 3D position determination module 56. This processing enables the 3D position determination module to identify 3D positions of corresponding points in pairs of images on the surface of a patient 20. This is achieved by the 3D position determination module 56 identifying corresponding points in pairs of images obtained by each stereoscopic camera 110 of the stereoscopic camera system 10 and then determining 3D positions for those points based on the relative positions of corresponding points in obtained pairs of images and stored data identifying the relative positions of cameras obtaining the images.

Typically the identification of corresponding points is based on analysis of image patches of around 16×16 pixels. In order to assist with identifying and matching corresponding patches as has been described each stereoscopic camera 110 of the stereoscopic camera system 10 includes a speckle projector 52 arranged to project a random or quasi random speckle pattern onto the patient 20 being imaged so that different portions of the surface of the patient 20 can be more easily distinguished. The size of the speckle pattern is selected so that different patterns will be apparent in different image patches.

The position data generated by the 3D position determination module 56 is then passed to the model generation module 58 which processes the position data to generate a 3D wire mesh model of the surface of a patient 20 imaged by the stereoscopic camera system 10. In this embodiment the 3D model comprises a triangulated wire mesh model where the vertices of the model correspond to the 3D positions determined by the 3D position determination module 56. When such a model has been determined it is stored in the generated model store 60.

When a wire mesh model of the surface of a patient 20 has been stored, the matching module 64 is then invoked to determine a matching translation and rotation between the generated model based on the current images being obtained by the stereoscopic camera system 10 and a previously generated model surface of the patient stored in the target model store 62. The determined translation and rotation can then be sent as instructions to the mechanical couch 18 to cause the couch to position the patient 20 in the same position relative to the treatment apparatus 16 as they were when they were previously treated.

Subsequently, the stereoscopic camera system 10 can continue to monitor the patient 20 and any variation in position can be identified by generating further model surfaces and comparing those generated surfaces with the target model stored in the target model store 62. If it is determined that a patient has moved out of position, the treatment apparatus 16 can be halted and the patient 20 repositioned, thereby avoiding irradiating the wrong parts of the patient 20.

In order to construct models of the surface of a patient with as great an accuracy as possible, the stereoscopic camera system 10 needs to be calibrated so that matching portions of images can be converted into a determination of 3D positions. This involves determining the relative positioning and orientation of the image detectors. Additionally the calibration of the stereoscopic camera system 10 must correct for any optical distortion introduced by the lenses 46 or any of the other internal characteristics of the underlying image detectors.

The applicants have appreciated that the accuracy of the monitoring system can be improved by implementing a two-stage calibration of stereoscopic camera system 10.

In conventional calibration methods, such as that described in U.S. Pat. Nos. 7,889,906 and 7,348,974, both the extrinsic camera parameters (i.e. the relative location and orientation of the image detectors) and the intrinsic camera parameters (i.e. defining the internal characteristics of the image detectors, such as the radial distortion, decentering/tangential distortion, focal length etc) are determined by a single-stage calibration process that involves imaging a calibration object located substantially at the iso-centre of the treatment apparatus, wherein the iso-centre is the point in space on which the radiation beam(s) generated by the treatment apparatus are focussed. However, the applicants have appreciated that determining the intrinsic camera parameters based on images of a calibration object at such a position is a cause of error.

During treatment, the surface of a patient is monitored whilst the radiation beam generated by the treatment apparatus is focussed at the iso-centre, where the tumour being treated is located. In most cases the tumour being treated is located within the patient's body, away from the surface being monitored. If the intrinsic parameters of the images detectors are determined based solely on imaging a calibration object positioned at the iso-centre, such parameters will not necessarily match with the parameters required to correct images for distortions at positions further away from the iso-centre. Thus in order to minimise error, rather than determining such correction factors solely based on images of a calibration object located at the iso-centre, the determination of the intrinsic parameters should take into account the expected location of the surface of a patient being monitored. This can be achieved by implementing a two-stage calibration of the stereoscopic camera system in which optical distortion parameters (i.e. intrinsic parameters defining the internal characteristics of the image detectors) and relative camera location parameters (i.e. extrinsic parameters) are determined relative to the expected location of the surface to be imaged, followed by an adaptation of the relative camera location parameters to account for the positions and orientations of the image detectors relative to the iso-centre of the treatment apparatus.

Figure 4:
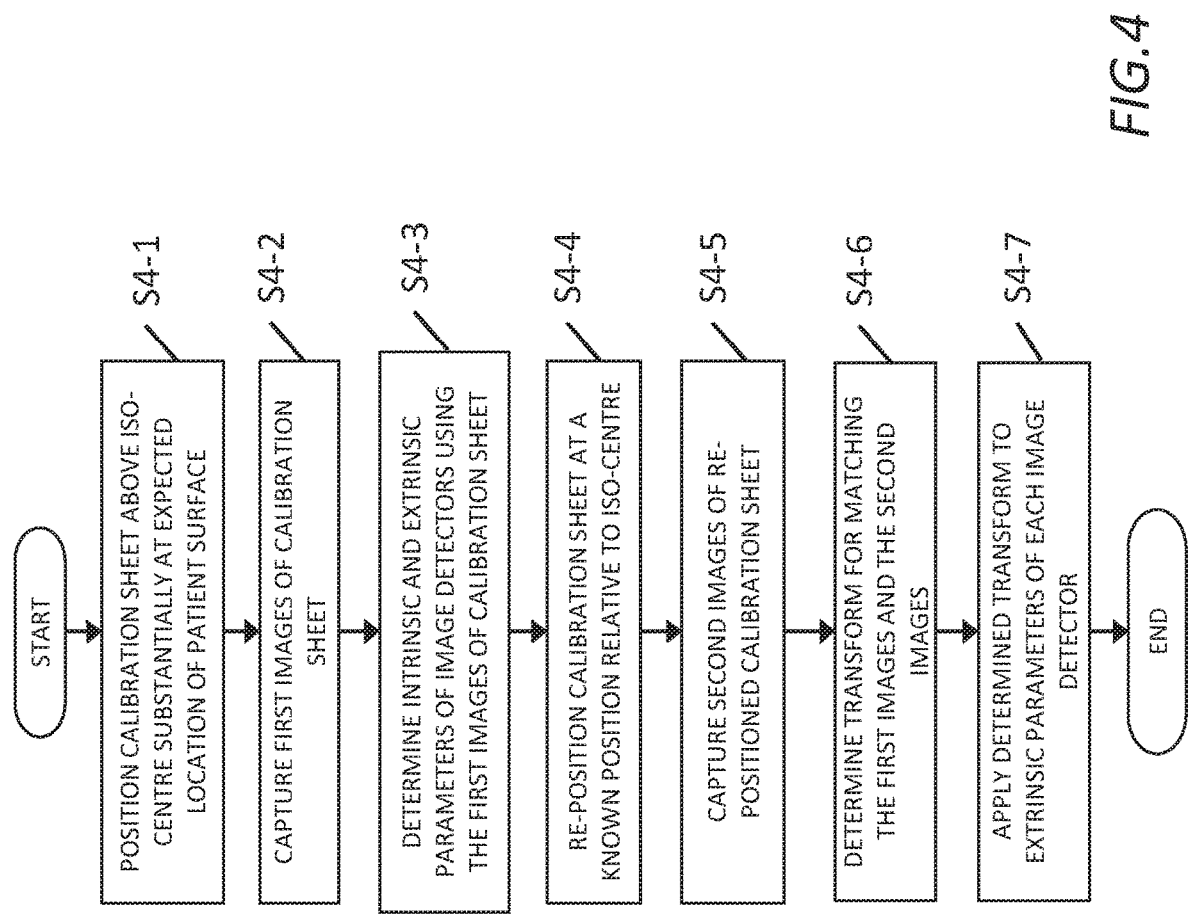
FIG. 4 is a flow diagram of a calibration method in accordance with the present invention.

FIG. 4 is a flow diagram illustrating the improved process of calibrating a stereoscopic camera system 10 in accordance with an embodiment of the present invention. In the first stage of the two-stage calibration process, the stereoscopic camera system 10 undergoes an initial calibration in which a calibration object, located at a position that corresponds with the average expected location of the surface of a patient lying on the couch for treatment (e.g. 5 to 10 cm above the identified iso-centre), is used to determine the relative camera locations and any image distortions arising from the image detectors. In particular, in this embodiment the calibration object is located above the iso-centre of the treatment apparatus 16 with the surface of calibration object being substantially over/vertically aligned with the iso-centre at the expected position of the surface of a patient during treatment.

Figure 5:
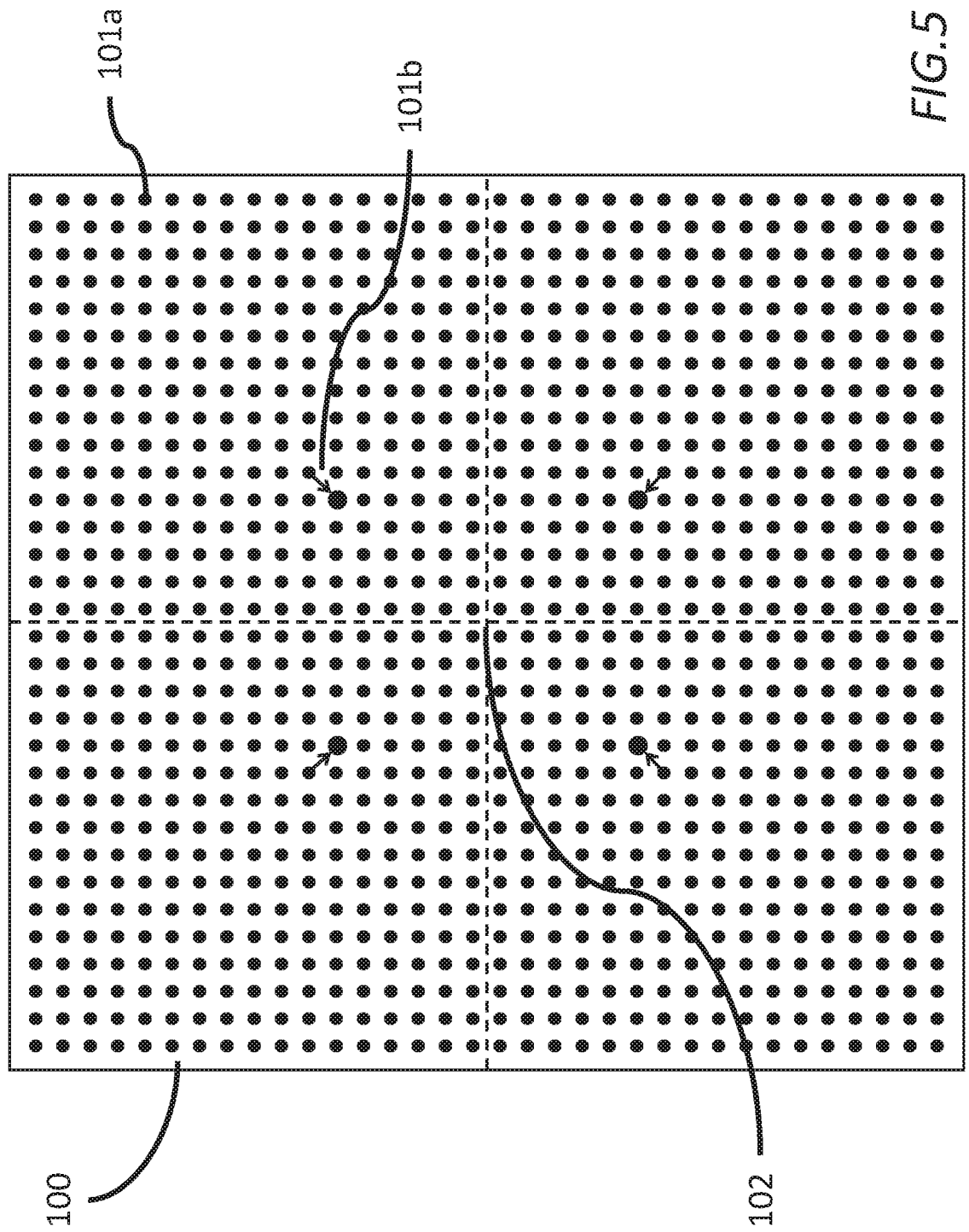
FIG. 5 is a plan view of an exemplary calibration object for use in the calibration method of FIG. 4.

FIG. 5 illustrates a plan view of an example of an exemplary calibration object. In this example, the calibration object is a calibration sheet 100 comprising a 70×70 cm sheet of flat rigid material such as aluminium or steel on which a pattern revealing a 34×32 matrix of markings/circles 101a at known positions on the surface of the sheet is provided. Additionally, towards the centre of the calibration sheet are four smaller markers 101b adjacent to four circles the centres of which together identify the four corners of a square of known size, and also a cross 102 formed by a pair of dashed lines which meet at the centre of the sheet 100.

The iso-centre is the focus of the radiation beam generated by the treatment apparatus 16; however, the ionising radiation used in radiotherapy is not in the visible region of the electromagnetic spectrum. This means it is hard to determine the location of the iso-centre unless some other means is provided.

In order to identify the location of the iso-centre of the treatment apparatus 16, many treatment rooms make use of a laser projection system that highlights the position of the iso-centre. If this is the case, then the location of the iso-centre can then be identified by positioning a calibration sheet 100 so that the laser light produced by the laser projection system just skims over the surface of the calibration sheet 100. The lines 102 on the calibration sheet 100 (see FIG. 5) are then aligned with the projected planes of laser light so that, as far as possible, the cross formed by the intersection of the lines 102 is located at the iso-centre as defined by the intersection of the planes of light projected by the laser light projectors. The location of the iso-centre can be identified by processing images of the calibration sheet 100 obtained by the image detectors to determine the position of the cross 102.

Alternatively, the method described in U.S. Pat. No. 7,348,974 might be used. In such a method, the position of the iso-centre is highlighted using a cross hair target projected from the end of the gantry 24. The position of the iso-centre is then determined by obtaining images of a calibration sheet 100 where the cross 102 is aligned with the cross hair target at two separate points along the path of the cross hair target projected from the gantry 24 and with the gantry 24 at two separate angles, so that the intersection of the lines joining the positions of the crosses 102 along the two paths can be used to identify the iso-centre.

Once the location of the iso-centre has been identified, the calibration sheet 100 is then located above the iso-centre of the treatment apparatus 16, at a position that corresponds with the average expected location of the surface of a patient lying on the couch for treatment (e.g. 5 to 10 cm above the identified iso-centre), with the calibration sheet being substantially over/vertically aligned with the iso-centre (S4-1). This can be achieved by positioning the calibration sheet on the mechanical couch 18 substantially aligned with any laser light system highlighting the location of the iso-centre. The mechanical couch can then be raised by an amount corresponding to the usual average distance between the iso-centre and the surface of a patient being monitored during treatment. A first set of images of the calibration sheet 100 are then obtained by all of the image detectors of the stereoscopic camera system 10 (S4-2) and stored in the memory of the computer 14.

This first set of images of the calibration sheet located at the expected position of the surface to be imaged are then processed to determine optical distortion and relative camera position parameters of the image detectors (S4-3).

Relative camera position parameters can be determined by identifying the positions of the four markers 101b within the images and their associated circles. This can be done either automatically using conventional techniques or alternatively, a user may identify the four circles manually. From the relative positions of circles identified by the markers 101b in the images, for each image a first projective transformation is determined which accounts for the estimated centres of the identified circles defining the corners of a projected distorted square in the image, wherein this perceived distortion of the square arises due to the relative orientation of the calibration sheet 100 and the image detector obtaining the image (i.e. perspective distortion). In this embodiment this first transformation determined is an estimated transformation for rectifying the perspective distorted image so that the circle centres correspond to the corners of a square.

The calculated transform is then utilised to determine estimated three-dimensional co-ordinates for the centres of each of the circles identified by the associated markers 101b. These calculated co-ordinates then identify an estimated location and orientation for the plane corresponding to the surface of the calibration sheet 100 relative to the position of the image detector from which the image has been obtained.

Each pixel in the image obtained by the image detector is then processed in turn to determine where within the plane containing the estimated positions of the circle centres, each pixel corresponds. The estimated circle centres are then processed in turn and the pixels in an image that correspond to points lying within a predetermined distance from each circle centre in the calculated plane are then identified. In this embodiment, these areas are selected to encompass points lying within the plane of the calibration sheet up to a distance slightly larger than the radius of the circles appearing on the calibration sheet. Thus in this way, for each circle, a set of pixels is identified which correspond to the appearance of a portion of the sheet centred on the estimated circle centre position and extending slightly beyond the outer edge of the circle in question.

The grey scale values for each of the pixels in each set are then utilised determine an improved estimate of the co-ordinates for the circle centres. For each pixel within a set identified for a particular circle, x and y co-ordinates are determined for the positions of the pixels in the estimated plane that corresponds to the surface of the calibration. These calculated x and y co-ordinates are then utilised to determine improved estimates of the x,y co-ordinates of the circle centre using the following equations:

$$x = \frac{\sum gx}{\sum g}$$

$$y = \frac{\sum gy}{\sum g}$$

where $\Sigma g$ is the sum of all pixel values in the set identified for a particular circle centre, $\Sigma gx$ is the sum of the grey scale pixel values for a pixel multiplied by the x co-ordinates for those pixels and $\Sigma gy$ is the sum of the grey scale pixel values for a pixel multiplied by the y co-ordinates for those pixels, and where the colour of the circle is associated with a high grey scale value and the colour of the background corresponding to the calibration sheet is associate with a low grey scale value.

Co-ordinates for the point within the image corresponding to the new estimated circle centres are then determined from these x,y co-ordinates and these updated estimates of the centres of the marked circles are then utilised to determine a more accurate estimated transformation for rectifying the perceived perspective distortion of the image of the calibration sheet. The above process can then be repeated until an accurate estimate of the actual circle centre positions is made and the true transform required to rectify the perceived perspective distortion of the image of the calibration sheet, and thereby account for the relative location and orientation of the calibration sheet, is determined.

Using the final determined transform, the expected positions of all of the circles on the sheet appearing in the image are then calculated, and the portions of the images in the vicinity of each of the estimated circle centres are then processed individually in the same way as described above. For each of the circles, a set of pixels is identified corresponding to points within a preset distance from the circle centre, and then an improved circle centre co-ordinate is calculated using the grey scale values and co-ordinate values as described above.

When the co-ordinates for the centres of each of the circles on the calibration sheet 100 have been calculated for an image, the relative orientation of the different image detectors can then be calculated from the relative positions of these points in the images and the known relative locations of these circles on the surface of the calibration sheet, as is described in detail in "A Versatile Camera Calibration Technique for High-Accuracy 3D Machine Vision Metrology Using Off the Shelf TV Cameras and Lenses", Roger Tsai, IEEE Journal of Robotics and Automation, Vol. Ra-3, No. 4, August 1987 which is hereby incorporated by reference. This information is then used to define the initial relative camera position parameters for each stereoscopic camera 110 of the stereoscopic camera system 10. For example, these initial relative camera position parameters can comprise three translations and three rotations necessary to transform the camera coordinate system into the coordinate system used by the patient monitoring system (i.e. a 3D rigid body transformation). The initial relative camera position parameters are then stored within a memory of the computer 14.

Figure 6A:
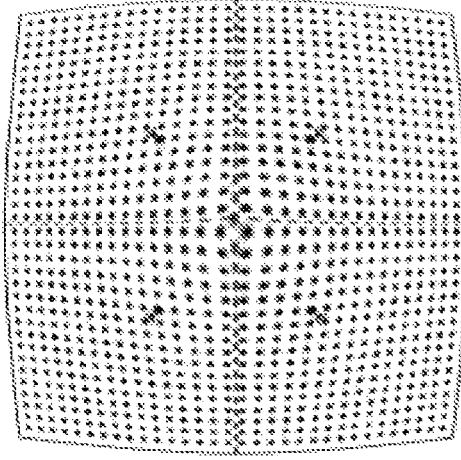
FIGS. 6A-C are illustrative examples of images of the calibration sheet of FIG. 5 illustrating the results of a number of different lens distortions.
Figure 6B:
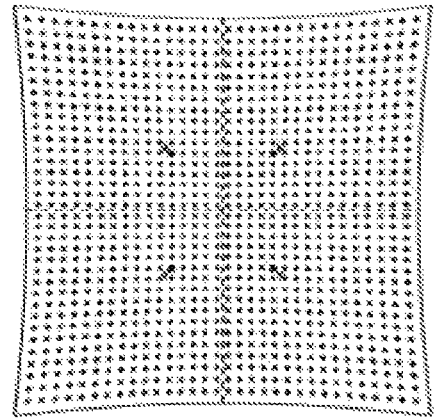
Figure 6C:
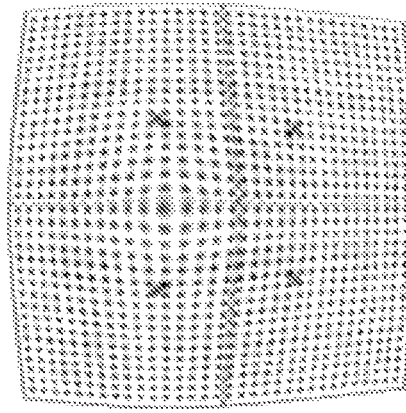

Based on the determined initial relative camera position parameters, the images of the calibration sheet obtained by the individual image detectors can be then be processed further in order to determine the optical distortion parameters. For example, this could be achieved by applying a 3D rigid body/affine transformation defined by the extrinsic parameters that accounts for the perceived perspective distortion arising due to the surface of the calibration sheet being viewed at an oblique angle. Having processed the images, the application of the determined transformation for each image should result in an image of the calibration sheet 100 that corresponds to a plan view of the calibration sheet 100, such as that illustrated in FIG. 5. However, in practice, optical distortions introduced by the image detectors will still be present in the transformed images. FIG. 6A illustrates an example of an image of the calibration sheet 100 in which barrel radial distortion is present, FIG. 6B illustrates an example of an image of the calibration sheet 100 in which pincushion radial distortion is present, and FIG. 6C illustrates an example of an image of the calibration sheet 100 in which de-centering distortion is present.

By identifying the locations and shapes of the circles 101a in the transformed images and comparing with the expected position and shapes of the circles on the calibration sheet 100, optical distortion parameters that account for the optical distortions (e.g. radial distortion, decentering/tangential distortion, etc.) introduced by the image detectors can be calculated and stored within a memory of the computer 14 for use in the subsequent generation of accurate three dimensional representations of the surface of a patient.

In the second-stage of the two-stage calibration process, the relative camera position parameters determined in the first-stage of the calibration are adapted to account for the positions and orientations of the image detectors relative to the iso-centre of the treatment apparatus.

When this second-stage of the calibration is to occur, the calibration sheet 100 is relocated to a position that is at a known location relative to the iso-centre of the treatment apparatus 16 (S4-4), for example substantially at the iso-centre. Again, this can be achieved by positioning the calibration sheet 100 on the mechanical couch 18 substantially aligned with any laser light system highlighting the location of the iso-centre. A second set of images of the calibration sheet 100 are then obtained by all of the image detectors of the stereoscopic camera system 10 (S4-5). This second set of images are then processed to determine a transform for matching the images of the calibration sheet located at the expected position of the surface to be imaged to the images of the calibration sheet located substantially at the iso-centre of the treatment apparatus 16 (S4-6). The determined transform is then applied to the initial relative camera position parameters that were previously determined for each of the plurality of image detectors of the stereoscopic camera system 10 during the first calibration stage (S4-7), so that the final camera position parameters can be determined relative to a co-ordinate position based on the location of the iso-centre of the treatment apparatus 16 and these final camera position parameters stored.

When the stereoscopic camera system 10 is comprised of a single stereoscopic camera, then the transform to be applied to the initial relative camera position parameters can be determined by comparing the co-ordinates of a set of points on the calibration sheet in the images of the calibration sheet located at the expected position of the surface to be imaged with the co-ordinates of this set of points on the calibration sheet in the images of the calibration sheet located substantially at the iso-centre of the treatment apparatus. For example, these points on the calibration sheet could be circles on the calibration sheet whose coordinates can be extracted from the images in accordance with the methods described above. This comparison would typically involve undertaking Procrustes analysis to determine a transformation which minimises the differences in position between the set of points in the first images captured by the stereoscopic camera and the set of points in the second images captured by the stereoscopic camera.

When the stereoscopic camera system 10 is comprised of a plurality of stereoscopic cameras, then an individual transform is determined for each of the stereoscopic cameras. Each of the individual transforms can be determined as described above. However, rather than applying the individual transforms to the image detectors of the corresponding stereoscopic camera, all of the individual transforms may be averaged, and the resulting average transform applied to all of the image detectors of the stereoscopic camera system (i.e. to all of the image detectors of each stereoscopic camera).

In this regard, the applicants have appreciated that the transform for translating between two different positions should be exactly the same for each stereoscopic camera. However, in practice, there are always some inaccuracies that will lead to differences between the individual transforms determined for each stereoscopic camera. Consequently, it has been found that if the transforms calculated for each individual stereoscopic camera are applied to the relative camera position parameters (i.e. the extrinsic parameters) calculated for the corresponding stereoscopic camera, then these inaccuracies introduce errors that cause the surfaces created from the images captured by the separate stereoscopic cameras to diverge. By determining and applying the average of the transforms to each stereoscopic camera, this approach ensures that the same transform is used for each stereoscopic camera, avoiding any divergence, whilst also making use of the average to apply a "best-fit" that should minimise any error.

Alternatively, a transform could be determined for just one of the plurality of stereoscopic cameras, and that transform applied to all of the stereoscopic cameras of the stereoscopic camera system 10. Whilst this would avoid any divergence, this approach is less likely to reduce the overall error.

In some embodiments of the above described two-stage calibration process it is possible to generate a set of pre-stored intrinsic and extrinsic parameters for the stereoscopic camera system. This would involve performing the first-stage of the calibration of the stereoscopic camera system at a series of different locations above the iso-centre (e.g. 75 mm above, 100 mm above etc). The set of intrinsic and extrinsic parameters determined relative to each location would then be stored in the memory of the computer 14, and the appropriate set selected when a surface is to be imaged. For example, when a patient is to be monitored, a random selection of one of the sets of intrinsic and extrinsic parameters that are stored in the system could be made, and the surface of the patient imaged using the selected set of intrinsic and extrinsic parameters. The captured images of the surface could then be used to determine the actual position of the surface to be imaged, and the set of intrinsic and extrinsic parameters corresponding to the determined position could then be selected from the sets pre-stored in the memory of the system. This would then allow the system to quickly select the most appropriate intrinsic and extrinsic parameters for a particular imaging scenario. In particular, by implementing a plurality of separate calibrations that each relate to a different expected location of the surface of a patient, it is possible to generate and store multiple sets of calibration data that cover a variety of different expected surfaces locations so that the most appropriate calibration parameters can be selected for a particular patient based on the actual location of the surface of the patient, and without necessarily needing to perform separate calibrations for each new patient.

As the intrinsic camera parameters are calculated for a position that should correspond approximately with the likely location of the surface of a patient during treatment, such parameters should be accurate for processing an image of a surface at this location. Thus, the inaccuracies that would arise from deriving such corrections based on the imaging of a calibration sheet positioned substantially at the iso-centre, which may not accurately correspond to correction factors for a position removed from the iso-centre, can be avoided. Therefore, in the two-stage calibration process described herein the calibration of the intrinsic parameters relative to the expected location of the surface being imaged provides the best accuracy. The extrinsic parameters are then transformed so that they are applicable to the iso-centre of the treatment apparatus.

In the system described above estimates of the co-ordinates of the centres of circles appearing on the surface of a calibration sheet are described as being identified on the basis of grey scale values where the colour of the circle is associated with a high grey scale value and the colour of the background corresponding to the calibration sheet is associate with a low grey scale value. It will be appreciated that such a result could be achieved by selecting the colouring of the calibration sheet so that this result was achieved. Alternatively, the colour selected for the circles on the calibration sheet could be selected to give rise to lower values than the background and image data could then be inverted prior to processing.

In the above described embodiment the determination of the positions of circle centres is described solely on the basis of processing grey scale images. It will be appreciated that initial estimates of circle centre positions could be calculated by thresholding the grey scale images and utilising the generated binary images to identify the initial estimate locations for the circle centres. Improved estimates could then be achieved by processing the grey scale images to take advantage of the additional information in such images to improve the accuracy of the circle centre estimates.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means. When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

The invention claimed is:

1. A method of calibrating a patient monitoring system including a plurality of image detectors arranged to view a surface of a patient lying on a mechanical couch of a radio therapy treatment apparatus, the method comprising:
    identifying an iso-centre of the treatment apparatus;
    performing a first calibration stage by:
        locating a calibration object at a first position where a visible surface of the calibration object substantially corresponds to an expected position of the surface of the patient lying on the mechanical couch of the radio therapy treatment apparatus during treatment, the first position being above the previously identified iso-centre of the treatment apparatus to account for a difference between the expected position of the patient lying on the mechanical couch and the iso-centre of the treatment apparatus; and
        obtaining images of the calibration object using the plurality of image detectors and processing the obtained images to ascertain relative locations and orientations of the plurality of image detectors and optical distortion parameters indicative of optical distortions present in the images of the calibration object obtained by the image detectors;
    performing a second calibration stage by:
        re-locating the calibration object to a second position at a known position relative to the iso-centre of the treatment apparatus; and
        obtaining images of the re-located calibration object using the plurality of image detectors and processing the obtained images to determine a transform corresponding to the relocation of the calibration object from the first position to the iso-centre of the treatment apparatus; and
    storing data indicative of optical distortions present in the images obtained by the image detectors of the calibration object in the first position during the first calibration stage, and data indicative of the locations and orientations of the image detectors relative to the iso-centre of the treatment apparatus determined by applying the determined transform obtained during the second calibration stage to the ascertained relative locations and orientations of the image detectors.

2. The method of claim 1, wherein the patient monitoring system-includes a single stereoscopic camera having a plurality of image detectors.

3. The method of claim 1, wherein the patient monitoring system includes a plurality of stereoscopic cameras each having a plurality of image detectors, wherein determining a transform corresponding to the relocation of the calibration object from the first position to the iso-centre of the treatment apparatus comprises:
    individually processing images from each the plurality of stereoscopic cameras to determine for each of the stereoscopic cameras, a transform corresponding to the re-location of the calibration object from the first position to the iso-centre of the treatment apparatus; and
    determining an average transform corresponding to the relocation of the calibration object from the first position to the iso-centre of the treatment apparatus.

4. The method of claim 1, wherein the patient monitoring system includes a plurality of stereoscopic cameras each having a plurality of image detectors, wherein determining a transform corresponding to the relocation of the calibration object from the first position to the iso-centre of the treatment apparatus comprises:
    processing images from one the plurality of stereoscopic cameras to determine a transform corresponding to the relocation of the calibration object from the first position to the iso-centre of the treatment apparatus.

5. The method of claim 1, wherein at the first position the calibration object is located 5 to 10 cm above the identified location of iso-centre of the radio therapy treatment apparatus.

6. The method of claim 1, wherein the patient monitoring system includes one or more lenses located between the patient and the image detector and, wherein determining lens distortion parameters indicative of optical distortions for each of the plurality of image detectors comprises:
    applying transformations that account for perspective distortions arising from the relative locations and orientations of the image detectors causing the image detectors to view the surface of a calibration object at an oblique angle; and
    comparing the transformed images to an expected image of the calibration object from a predefined viewpoint to identify optical distortions.

7. The method of claim 6, wherein the calibration object includes a calibration sheet having markings located in a known pattern, wherein the step of comparing the transformed images to an expected image of the calibration object to identify optical distortions comprises:
    processing the transformed images to identify locations of markings present on the calibration sheet and comparing with the positions of the markings in the expected image of the calibration sheet viewed from a predefined viewpoint.

8. A method of operating a patient monitoring system including a plurality of image detectors arranged to view the surface of a patient lying on a mechanical couch of a radio therapy treatment apparatus, the method comprising:
    implementing a plurality of calibrations of the patient monitoring system, the calibrations being done by:
    identifying an iso-centre of the treatment apparatus;
    performing a first calibration stage by:
        locating a calibration object at a first position where a visible surface of the calibration object substantially corresponds to an expected position of the surface of the patient lying on the mechanical couch of the radio therapy treatment apparatus during treatment, the first position being above the previously identified iso-centre of the treatment apparatus to account for a difference between the expected position of the patient lying on the mechanical couch and the iso-centre of the treatment apparatus; and
        obtaining images of the calibration object using the plurality of image detectors and processing the obtained images to ascertain relative locations and orientations of the plurality of image detectors and optical distortion parameters indicative of optical distortions present in the images of the calibration object obtained by the image detectors;

performing a second calibration stage by:
re-locating the calibration object to a second position at a known position relative to the iso-centre of the treatment apparatus; and
obtaining images of the re-located calibration object using the plurality of image detectors and processing the obtained images to determine a transform corresponding to the relocation of the calibration object from the first position to the iso-centre of the treatment apparatus; and storing data indicative of optical distortions present in the images obtained by the image detectors of the calibration object in the first position during the first calibration stage, and data indicative of the locations and orientations of the image detectors relative to the iso-centre of the treatment apparatus determined by applying the determined transform obtained during the second calibration stage to the ascertained relative locations and orientations of the image detectors, wherein each of the plurality of calibrations is implemented with the calibration object located at a different first position, and the data stored as a result of each of the plurality of calibrations further comprises an indication of the location of the first position used for the calibration;

determining an actual position of a visible surface of the patient;

selecting the data stored as a result of the calibration for which the location of the first position used for the calibration corresponds to the actual position of the surface of the patient;

obtaining images of a patient lying on the mechanical couch of the radio therapy treatment apparatus using the plurality of image detectors; and generating a model of the surface of the patient lying on the mechanical couch of the radio therapy treatment apparatus utilizing the obtained images and the selected data.

9. A method of monitoring a patient, the method comprising:
calibrating a patient monitoring system including a plurality of image detectors arranged to view a surface of a patient lying on a mechanical couch of a radio therapy treatment apparatus, the calibrating being done by:
identifying an iso-centre of the treatment apparatus;
performing a first calibration stage by:
locating a calibration object at a first position where a visible surface of the calibration object substantially corresponds to an expected position of the surface of the patient lying on the mechanical couch of the radio therapy treatment apparatus during treatment, the first position being above the previously identified iso-centre of the treatment apparatus to account for a difference between the expected position of the patient lying on the mechanical couch and the iso-centre of the treatment apparatus; and
obtaining images of the calibration object using the plurality of image detectors and processing the obtained images to ascertain relative locations and orientations of the plurality of image detectors and optical distortion parameters indicative of optical distortions present in the images of the calibration object obtained by the image detectors;

performing a second calibration stage by:
re-locating the calibration object to a second position at a known position relative to the iso-centre of the treatment apparatus; and
obtaining images of the re-located calibration object using the plurality of image detectors and processing the obtained images to determine a transform corresponding to the relocation of the calibration object from the first position to the iso-centre of the treatment apparatus; and storing data indicative of optical distortions present in the images obtained by the image detectors of the calibration object in the first position during the first calibration stage, and data indicative of the locations and orientations of the image detectors relative to the iso-centre of the treatment apparatus determined by applying the determined transform obtained during the second calibration stage to the ascertained relative locations and orientations of the image detectors;

obtaining images of the patient lying on a mechanical couch of a radio therapy treatment apparatus using the plurality of image detectors; and generating a model of the surface the patient lying on the mechanical couch of the radio therapy treatment apparatus-utilizing the obtained images and the stored data indicative of optical distortions present in images obtained by the image detectors, and data indicative of the locations and orientations of the image detectors relative to the iso-centre of the treatment apparatus.

* * * * *